United States Patent
Chinea et al.

(10) Patent No.: US 7,900,577 B2
(45) Date of Patent: Mar. 8, 2011

(54) SYSTEM AND A METHOD FOR STARCH-BASED, SLOW-RELEASE ORAL DOSAGE FORMS

(75) Inventors: Vanessa I. Chinea, Aguadilla, PR (US); Tienteh Chen, San Diego, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1957 days.

(21) Appl. No.: 10/832,702

(22) Filed: Apr. 27, 2004

(65) Prior Publication Data

US 2005/0238697 A1 Oct. 27, 2005

(51) Int. Cl.
*B05C 5/02* (2006.01)

(52) U.S. Cl. .............. 118/300; 118/24; 118/323; 347/2; 347/100

(58) Field of Classification Search .............. 118/323, 118/300; 347/2, 100; 427/2.14, 2.16, 2.21, 427/421.1
See application file for complete search history.

(56) References Cited

U.S. PATENT DOCUMENTS

| 3,934,006 | A | * | 1/1976 | Frommer et al. ............. 424/115 |
|---|---|---|---|---|
| 4,485,117 | A | | 11/1984 | Hudson et al. |
| 5,464,642 | A | * | 11/1995 | Villagran et al. ............. 426/439 |
| 5,801,116 | A | | 9/1998 | Cottrell et al. |
| 5,858,398 | A | * | 1/1999 | Cho ............................. 424/450 |
| 5,894,841 | A | | 4/1999 | Voges |
| 6,015,570 | A | | 1/2000 | Tucci et al. |
| 6,114,022 | A | | 9/2000 | Warner et al. |
| 6,271,001 | B1 | | 8/2001 | Clarke et al. |
| 6,326,015 | B1 | | 12/2001 | Tucci et al. |
| 6,350,594 | B1 | | 2/2002 | Clarke et al. |
| 6,607,744 | B1 | | 8/2003 | Ribi |
| 6,632,510 | B1 | | 10/2003 | Waller, Jr. et al. |
| 6,677,007 | B1 | | 1/2004 | Warner et al. |
| 2002/0135651 | A1 | * | 9/2002 | Spurgeon et al. ............. 347/100 |
| 2003/0075106 | A1 | * | 4/2003 | Lee et al. ...................... 118/663 |

FOREIGN PATENT DOCUMENTS

| EP | 1 413 434 | 4/2004 |
|---|---|---|
| EP | 1 452 170 | 9/2004 |
| WO | WO 2004/103337 | 12/2004 |

OTHER PUBLICATIONS

Stimpson; "Parallel Production of Oligonucleotide Arrays Using Membranes and Reagent Jet Printing"; Biotechniques, Eaton Publishing, vol. 25, No. 5, Nov. 1998, pp. 886-890.

* cited by examiner

*Primary Examiner* — Laura Edwards

(57) ABSTRACT

A system for producing a slow release oral dosage of medication includes a starch based media, and an oral dosage formulation jetted onto the starch based media.

27 Claims, 6 Drawing Sheets

SYSTEM AND A METHOD FOR STARCH-BASED, SLOW-RELEASE ORAL DOSAGE FORMS

BACKGROUND

Traditional oral dosage drug formulations include both active pharmaceutical ingredients (API) and inactive ingredients. The inactive ingredients (also called excipients), are components of the final formulation of a drug that are not considered active pharmaceutical ingredients (API) in that they do not directly affect the consumer in the desired medicinal manner. Traditional oral dosage forms have several inactive ingredients. Among the traditional inactive ingredients included in oral dosage forms are binders that hold the tablet together, coatings configured to mask an unpleasant taste, disintegrants configured to make the tablet break apart when consumed, enteric coatings, fillers that assure sufficient material is available to properly fill a dosage form, enhancers configured to increase stability of the active ingredients, preservatives aimed at preventing microbial growth, and the like.

The above-mentioned inactive ingredients have also been used to develop controlled release oral dosage solid formulations. These controlled release oral dosage solid formulations are designed to temporally control the release of the API from the oral dosage drug formulation. This temporal control allows for a time delayed release, or an extended release of a desired API formulation. The selection and optimization of the inactive ingredients to obtain an oral dosage solid form with the desired controlled release properties is both a complex and a lengthy process.

In addition to the complexity and difficulty traditionally associated with selecting and optimizing inactive ingredients to obtain an oral dosage solid form with controlled release properties, there are a number of highly insoluble drugs that are not well suited to sustained or controlled delivery. The formulation of these highly insoluble APIs into controlled or modified-release dosage forms using traditional formulation methods is both expensive and challenging due to the APIs' insolubility.

SUMMARY

A system for producing a slow release oral dosage of medication includes a starch based media, and an oral dosage formulation jetted onto the starch based media.

BRIEF DESCRIPTION OF THE DRAWINGS

The accompanying drawings illustrate various embodiments of the present system and method and are a part of the specification. The illustrated embodiments are merely examples of the present system and method and do not limit the scope thereof.

Throughout the drawings, identical reference numbers designate similar, but not necessarily identical, elements.

DETAILED DESCRIPTION

A number of exemplary systems and methods for producing a slow-release oral dosage form are disclosed herein. More specifically, an oral drug formulation is jetted onto an edible starch based media to form an extended release dosage form. The edible starch-based media may also be coated with a polymer to further modify the release rate of an oral drug formulation jetted thereon.

As used in the present specification and the appended claim, the term "edible" is meant to be understood broadly as any composition that is suitable for human consumption and is non-toxic. Similarly, the phrase "suitable for human consumption" is meant to be understood as any substance that complies with applicable standards such as food, drug, and cosmetic (FD&C) regulations in the United States and/or Eurocontrol experimental centre (E.E.C.) standards in the European Union. Additionally, the term "ink" is meant to be understood broadly as meaning any jettable fluid configured to be selectively emitted from an inkjet dispenser, regardless of whether it contains dye or any other colorant. The term "jettable" is meant to be understood both in the present specification and in the appended claims as any material that may be selectively deposited by any digitally addressable inkjet material dispenser.

In the following description, for purposes of explanation, numerous specific details are set forth in order to provide a thorough understanding of the present system and method for producing a slow-release oral dosage form. It will be apparent, however, to one skilled in the art, that the present method may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Exemplary Structure

Figure 1:
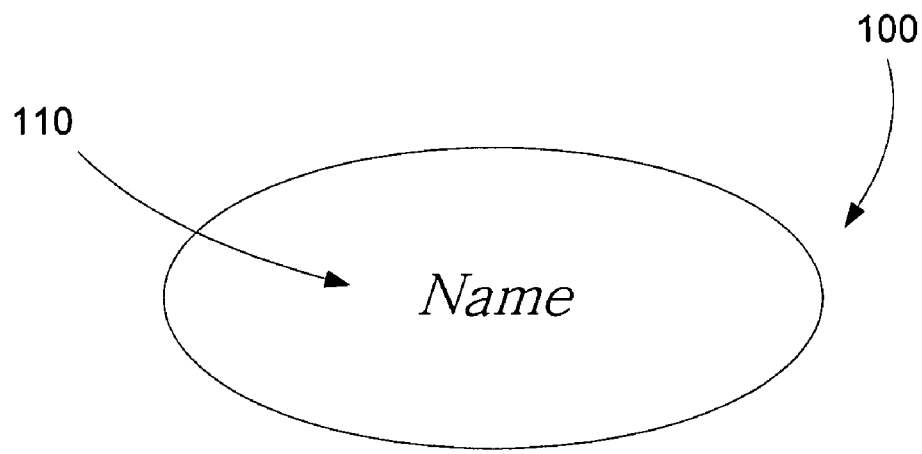
FIG. 1 is a perspective view of a traditional solid drug formulation, according to teachings of the prior art.

FIG. 1 illustrates a traditional solid oral drug formulation (100). As shown in FIG. 1, the traditional solid oral drug formulation (100) is a powder composition formed in the shape of a pill or a capsule. Often a name or other marking (110) is placed on the traditional solid drug formulation (100) to indicate source, identify chemical makeup, and/or to indicate a dosage. As noted above, the traditional solid oral drug formulations (100) have been formed with a number of inactive ingredients to produce controlled or modified-release dosage forms. However, as explained above, the selection and optimization of the inactive ingredients to obtain a solid oral dosage form with desired properties is a complex and lengthy process.

According to the present exemplary system and method, two dimensional substrates in the form of paper-like media can replace the use of powders as inactive ingredients in the oral dosage solid form. Consequently, the paper-like media can be used in combination with inkjet technology to produce oral dosage solid forms of drugs without the complex and costly manufacturing process mentioned above. According to the present system and method, an edible starch based media (such as rice paper) in combination with an inkjet dispenser is used to produce an extended released oral drug formulation.

Figure 2:
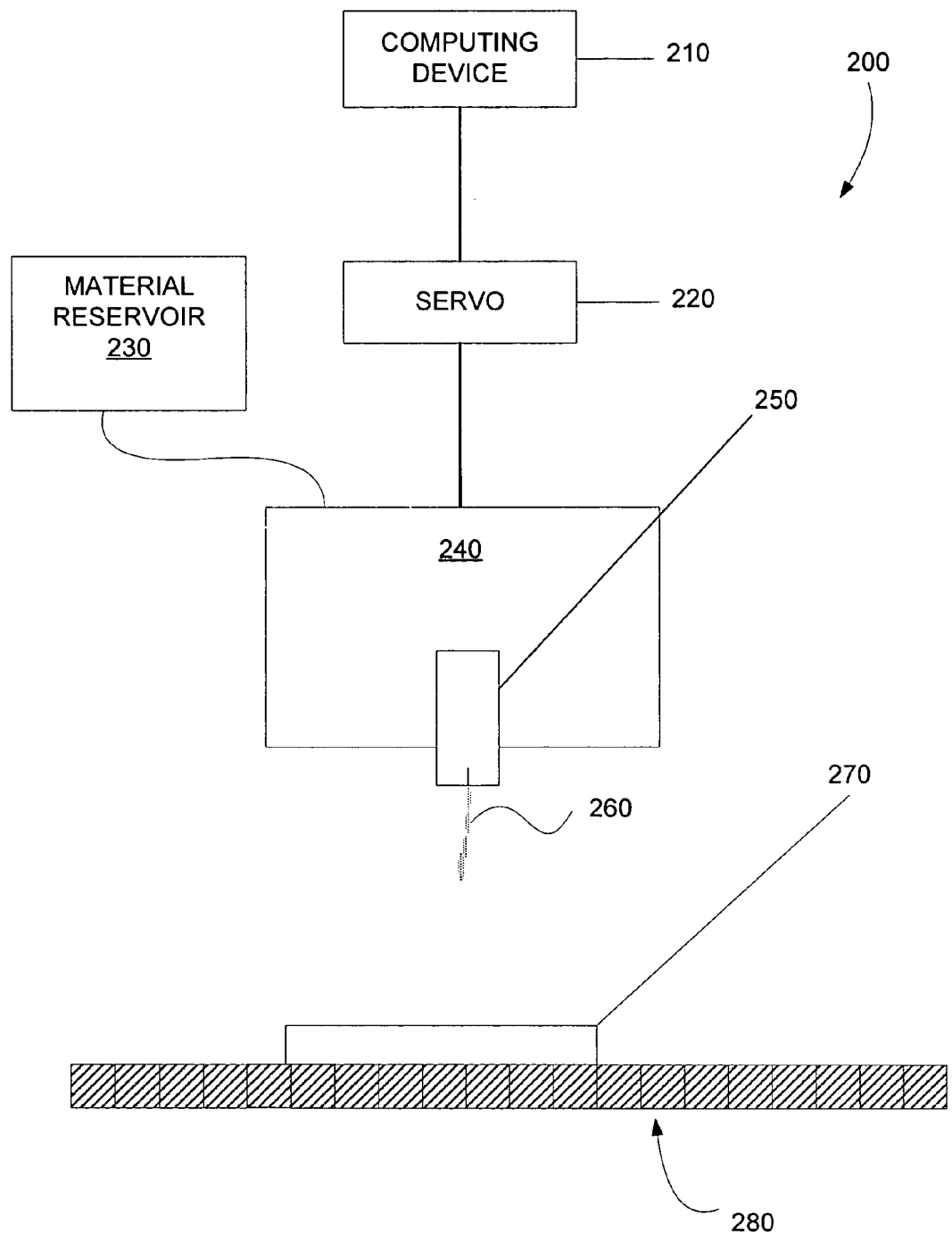
FIG. 2 is a simple block diagram illustrating a system that may be used to deposit an oral drug formulation onto a starch based media, according to one exemplary embodiment.

FIG. 2 illustrates an exemplary system (200) that may be used to apply an oral drug formulation (260) to a starch based media (270) according to one exemplary embodiment. As shown in FIG. 2, the present system includes a computing device (210) controllably coupled through a servo mechanism (220) to a moveable carriage (240) having an inkjet dispenser (250) disposed thereon. A material reservoir (230) is also coupled to the moveable carriage (240), and consequently to the inkjet print head (250). A substrate (280) is located adjacent to the inkjet dispenser (250) having a starch based media (270) disposed thereon. The above-mentioned components of the present system will now be described in further detail below.

The computing device (210) that is controllably coupled to the servo mechanism (220), as shown in FIG. 2, controls the selective deposition of an oral drug formulation (260) onto the starch based media (270). According to one exemplary embodiment, a representation of a desired quantity or dosage of the oral drug formulation (260) may be generated on an application hosted by the computing device (210). That representation may then be converted into servo instructions that are then housed in a processor readable media (not shown). When accessed by the computing device (210), the instructions housed in the processor readable media may be used to control the servo mechanisms (220) as well as the movable carriage (240) and inkjet dispenser (250), causing them to selectively deposit an oral drug onto the starch based media (270). The computing device (210) illustrated in FIG. 2 may be, but is in no way limited to, a workstation, a personal computer, a laptop, a personal digital assistant (PDA), or any other processor containing device.

The moveable carriage (240) of the present printing system (200) illustrated in FIG. 2 is a moveable material dispenser that may include any number of inkjet material dispensers (250) configured to dispense the present oral drug formulation (260). The moveable carriage (240) may be controlled by a computing device (210) and may be controllably moved by, for example, a shaft system, a belt system, a chain system, etc. making up the servo mechanism (220). As the moveable carriage (240) operates, the computing device (210) may inform a user of operating conditions as well as provide the user with a user interface.

As a desired quantity of the oral drug formulation (260) is printed on the starch based media (270), the computing device (210) may controllably position the moveable carriage (240) and direct one or more of the inkjet dispensers (250) to selectively dispense the oral drug formulation at predetermined locations on the starch based media as digitally addressed drops, thereby forming a desired dosage. The inkjet material dispensers (250) used by the present printing system (100) may be any type of inkjet dispenser configured to perform the present method including, but in no way limited to, thermally actuated inkjet dispensers, mechanically actuated inkjet dispensers, electro-statically actuated inkjet dispensers, magnetically actuated dispensers, piezo-electrically actuated inkjet dispensers, continuous inkjet dispensers, etc. Additionally, the ink-jet material dispenser can be heated to assist in dispensing the oral drug formulation. Moreover, the present oral drug formulation can be distributed using any number of printing processes including, but in no way limited to, inkjet printing, lithography, screen printing, gravure, and flexo printing.

The material reservoir (230) that is fluidly coupled to the inkjet material dispenser (250) houses the present oral drug formulation (260) prior to printing. The material reservoir may be any sterilizeable container configured to hermetically seal the oral drug formulation (260) prior to printing and may be constructed of any number of materials including, but in no way limited to metals, plastics, composites, ceramics, or appropriate combinations thereof.

FIG. 2 also illustrates the components of the present system that facilitate reception of the oral drug formulation (260) on the starch based media (270). As shown in FIG. 2, a substrate (280) may transport and/or positionally secure a starch based media (270) during a printing operation. The formation and composition of the oral drug formulation (260) and the starch based media (270) will now be described in detail below.

Exemplary Composition

According to one exemplary embodiment, the present system and method may be performed by selectively depositing the above-mentioned oral drug formulation (260) onto a starch based media (270). The starch based media (270) may include, but is in no way limited to, polymeric and/or paper organic film formers. Nonlimiting examples of such substrates include starch (natural and chemically modified), glycerin based sheets with or without a releasable backing, and the like; proteins such as gelatin, wheat gluten, and the like; cellulose derivatives such as hydroxypropylmethylcellulose, methocel, and the like; other polysaccharides such as pectin, xanthan gum, guar gum, algin, pullulan (an extracellular water-soluble microbial polysaccharide produced by different strains of Aureobasidium pullulans), and the like; sorbitol; seaweed; synthetic polymers such as polyvinyl alcohol, polymethylvinylether (PVME), poly-(2-ethyl 2-oxazoline), polyvinylpyrrolidone, and the like. Further examples of edible delivery substrates are those that are based on milk proteins, rice paper, potato wafer sheets, and films made from restructured fruits and vegetables. It should be understood that one or more of the above listed substrate materials, as well as additional materials included to modify the dissolution rates, may be used in combination in some embodiments. While the starch based media incorporated by the present system and method may take a number of different forms including, but in no way limited to, a paper made from a functional derivative of starch such as cross-linked, oxidized, acetylated, hydroxypropylated, carboxymethylated, and partially hydrolyzed starch; or a modified edible polysaccharide film made of cellulose derivates, starch hydrolysates, alginates, and/or carragenan; the present system and method will be described, for ease of explanation only, in the context of a rice based paper. Rice based paper is an edible starch based material which, according to one exemplary embodiment, includes potato starch fibers, water, and vegetable oil.

Figure 3A:
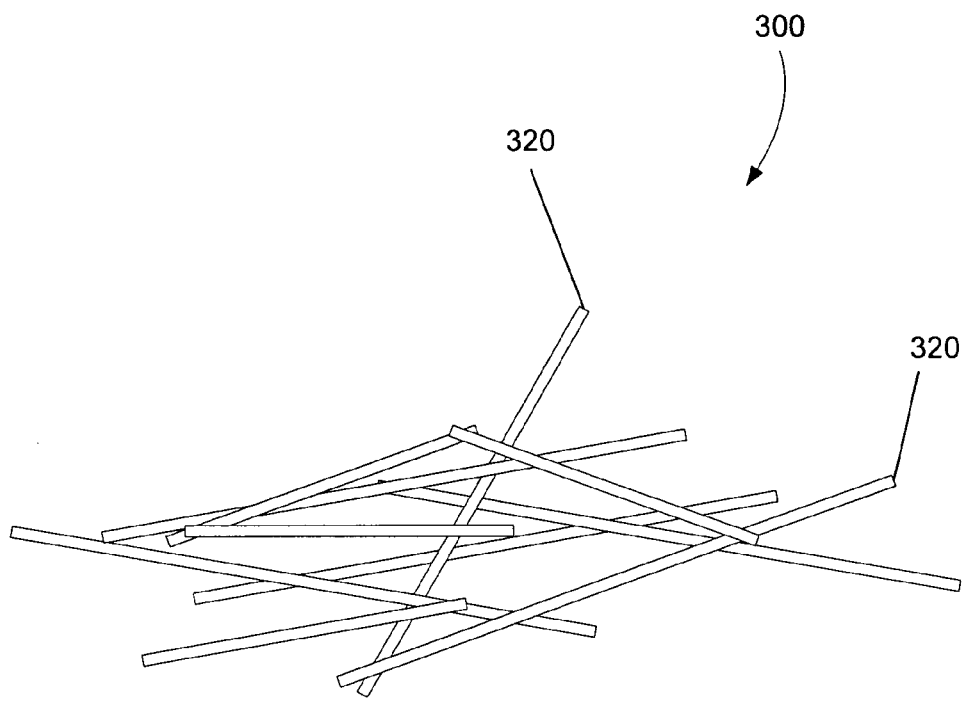
FIG. 3A is simple magnified view of a starch based media, according to one exemplary embodiment.

FIG. 3A illustrates a magnified view of an uncoated starch based media (300) according to one exemplary embodiment. As illustrated in FIG. 3A, the uncoated starch based media (300) is made up of a number of interlocking starch based fibers (320). The starch based fibers (320) that make up the uncoated starch based media (300) is made essentially of soluble starch. The soluble starch is comprised of glucose units linked together by oxygen bridges called glycosides. The glucose molecules in the starch based fibers (320) are oriented in an alpha orientation rather than a beta orientation as in cellulose. As a consequence of the alpha orientation, the starch based fibers (320) are more readily soluble in water and more easily digested by bacteria and other living organisms than cellulose. Additionally, the starch based fibers (320) are configured to absorb an oral drug formulation (260; FIG. 2) or any other API disposed thereon. Once the starch based fibers (320) absorb an oral drug formulation (260; FIG. 2) or any other API disposed thereon, the oral drug formulation is retained therein until a dissolution of the starch based fibers (320) occurs causing a release of the drug formulation.

Figure 3B:
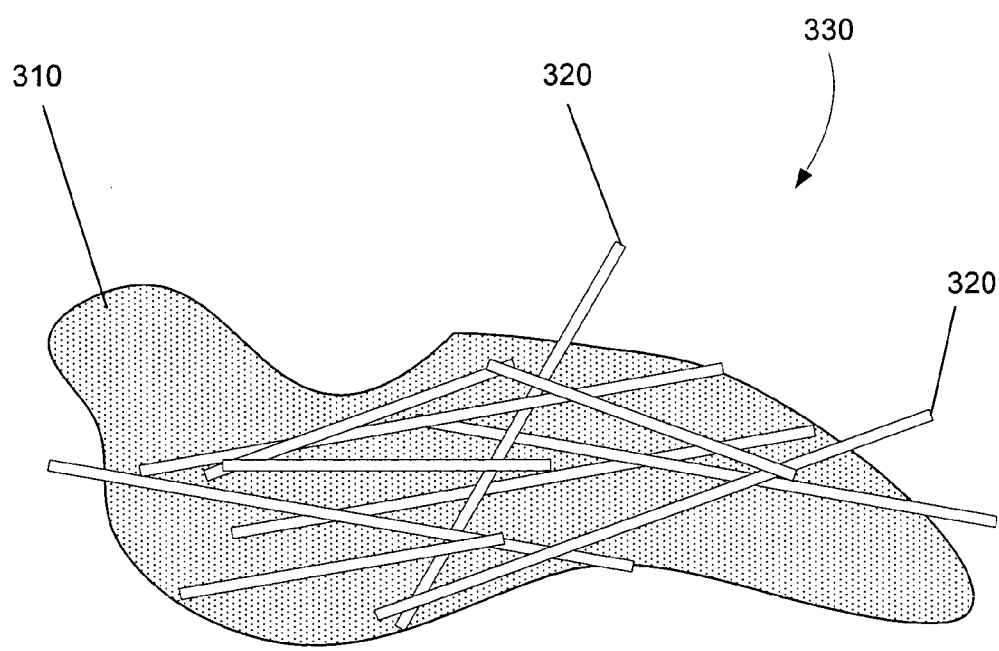
FIG. 3B is a simple magnified view of a coated starch based media, according to one exemplary embodiment.

According to another exemplary embodiment, illustrated in FIG. 3B, the starch based media (270; FIG. 2) used to receive the oral drug formulation (260; FIG. 2) is a coated starch based media (330). As shown in the magnified view of FIG. 3B, the coated starch based media (330) also includes a number of interlocked starch based fibers (320) as described above. However, according to the exemplary embodiment illustrated in FIG. 3B, there is also a coating (310) surrounding the interlocking starch based fibers (320). The coating (310) illustrated in FIG. 3B modifies the rate of water uptake and subsequent dissolution of the starch based fibers (320). Additionally, the coating (310) selected to cover the starch based fiber (320) may absorb a portion of the oral drug formulation (260; FIG. 2). Consequently, the rate of dissolution of the coating (310) when consumed, will affect the rate of release of an oral drug formulation (260; FIG. 2) as will be further detailed below with reference to FIG. 5. The coating (310) selected to coat the starch based fibers (320) may be any edible polymer including, but in no way limited to homopolymer of polyvinylphenol (PVP), copolymer of PVP and polyvinylacetate, crosslinked PVP particles, copolymer of PVP and polyvinylacetate, Cationic PVP, polyvinyl acetate (PVA) and PVA-polyethylene oxide (PEO) copolymer, PVA-vinylacetal copolymer, PVA-vinylacetal, PVA-vinylamine copolymer, poly vinyl methyl ether (PVME) homopolymer, hydroxypropylmethylcellulose, poly(2-ethyl oxazoline), gelatin, and methyl cellulose.

According to one exemplary embodiment of the present system and method, the above-mentioned starch based media (270; FIG. 2) receives an oral drug formulation (260; FIG. 2) to form a solid drug dosage. The oral drug formulation (260) illustrated in FIG. 2 that is selectively deposited onto the starch based media (270; FIG. 2) includes both an oral drug component and a jettable vehicle component, as illustrated below.

The oral drug component of the oral drug formulation (260) includes the desired API that forms a desired drug dosage. While the present system and method is exceptionally suited for traditionally insoluble oral drug components, any number of oral drug components may be incorporated by the present exemplary system and method including, but in no way limited to, Prednisolone, Glyburide, Lovastatin, Digoxin, and/or Nifedipine. Additionally, according to one exemplary embodiment, the oral drug component of the oral drug formulation (260) may include, but is in no way limited to, ace inhibitors, antianxiety medications, antihypertensive medications, blood glucose regulators, alzheimer-type dementia medications, anorexiants/central nervous system (CNS) stimulants, antidiuretics, specific antidotes, antihistamines, antipsychotics/antimanic medications, beta blockers, calcium channel blockers, contraceptives, dermatologics, diuretics, estrogens/progestins, entrapyramidal movement disorders (and hyperprolactinemia), and sedatives/hypnotics.

Examples of the above mentioned oral drug components of the oral drug formulation (260) include, but are in no way limited to, triazolam, felodipine, trandolapril, pergolide, rivastigmine tartrate, sibutramine hydrochloride, desmopressin acetate, flumazenil, desloratadine, risperidone, carvedilol, isradipine, norgestimate, methoxsalen, metolazone, estradiol, estrogens, conjugated estrogent, esterified cabergoline, zaleplon, and zolpidem tartrate.

In addition to the above-mentioned oral drug component, the present oral drug formulation (260; FIG. 2) includes a jettable vehicle component configured to provide properties to the oral drug formulation enabling the deposition of the oral drug formulation from an inkjet dispensing device. According to one exemplary embodiment, the jettable vehicle component of the oral drug formulation (260; FIG. 2) includes, but is in no way limited to, an edible solvent, surfactants, and/or humectants. Solvents and/or surfactants may be added to the oral drug formulation (260; FIG. 2) to enhance the jettable properties of the jettable oral drug formulation. Additional additives such as humectants can also be added to the jettable oral drug formulation to improve the reliability of an associated inkjet dispenser by reducing the likelihood of clogged nozzles.

The edible solvent component of the jettable vehicle component is included in the present oral drug formulation (260) for dispersion and transport of the oral drug component as well as any other additives. The vehicle solvent imparts a jettable viscosity to the oral drug formulation (260) while also evaporating at a rate sufficient to make a desired dosage resistant to smudging soon after it is deposited on a starch based media (270). According to one exemplary embodiment, the solvent comprises water, thus creating a water-based vehicle. In addition to low cost, water is effective as a solvent for many additives, greatly reduces inkjet dispenser compatibility issues, effectively suspends oral drug formulations and colorants, and effectively controls drying rates of the oral drug formulation. More specifically, a water-based vehicle may comprise from 20% by volume water up to about 90% by volume water. In another exemplary embodiment, the solvent component of the ink vehicle includes a mixture of water and an alcohol, such as ethyl alcohol. The addition of an alcohol to a solvent affects the viscosity and drying rate of the oral drug formulation, as well as acting as a surfactant.

Surfactants and emulsifiers may be added to the solvent component of the present oral drug formulation (260) in order to facilitate dispersion and/or dissolution of the oral drug component and any other additive in the solvent. Appropriate edible surfactant classes include, but are in no way limited to, lecithin, lecithin derivatives, glycerol esters, sorbitan derivatives, glycerol lactoesters of fatty acids, and ethoxylated fatty esters and oils. Examples of the above-mentioned classes include, but are in no way limited to, glycerol monolaurate, glycerol mono/dioleate, glycerol mono/diricinoleate, glycerol distearate, propylene glycerol dicaprylate/dicaprate, diethyleneglycol monolaurate, diethylene glycol monostearate, Decaglycerol mono/dioleate, triglycerol monoleate, hexaglycerol dioleate, hexaglycerol distearate, decaglycerol tetraoleate, decaglycerol decaoleate, Ethoxylated mono and diglycerides, polyoxyethylene (20) sorbitan monostearate, polyoxyethylene (20) sorbitan tristearate, polyoxyethylene (20) sorbitan monooleate, Polyoxyethylene 20 sorbitan monolaurate, Polyoxyethylene 20 sorbitan monooleate, Polyoxyethylene 20 sorbitan monostearate, Polyoxyethylene 5 sorbitan monooleate, Polyoxyethylene sorbitan trioleate, Polyoxyethylene 20 sorbitan tristearate, acetylated monoglycerides, citric acid esters of monoglycerides, lactic acid esters of monoglycerides, polglycerol esters of fatty acids, propylene glycol esters of fatty acids, soorbitan esters of fatty acids, sodium stearoyl lacylates, mono and diglycerides with polysorbate 80, mono and diglycerides with polysorbate 65, citric ester of monoglycerides, citric and lactic mixed ester of monoglycerides, glycerol mono/diester of isostearic and succinic acid, glycerol mono/diester of palmitic/stearic acid and sodium stearate, diacetylated tartaric acid of ester of monglycerides, sorbitan tnonolaurate, PEG-10 sorbitan monolaurate, polysorbate 20, polysorbate 60, polysorbate 80, sorbitan monoleate, polysorbate 80, sorbitan monopalmitate, sorbitan sesquiolate, sorbitan triolate, sorbitan tristearate, POE-20 monolaurate, POE-20 sorbitan monostearate, POE-20 sorbitan tristearate, and POE-20 sorbitan monoleate. Exemplary trade names for the above-mentioned surfactants include, but are not limited to, ALCOLEC, ALDO CALGENE CAPMUL CENTROL, CENTROLENE, CENTROLEX, CENTROMIX, CENTROMIX, DREWPOL, DURFAX, DURTAN, DURLAC, DUR-LO, GLYCOSPERSE GRINDSTED, ICE, IMWITOR, LIPOSORB, MAZOL, SPAN, T-MAZ, and TWEEN 20, 60, 65, or 80. According to one exemplary embodiment, a surfactant or emulsifier may be present in a concentration of up to about 20% by volume of the ink vehicle. In one particular embodiment, the surfactant or emulsifier comprises ethyl alcohol in a concentration of about 13% to about 20% by weight of the vehicle.

A humectant may also be included in the present jettable vehicle component to control the moisture content and viscosity of the resulting oral drug formulation (260). The ink vehicle typically dries and is absorbed once it is disposed on the starch based media (270) or other substrate surface; however, drying prior to printing decreases viscosity and thus may inhibit the jettability of the oral drug formulation (260). Therefore, a humectant may be included in the vehicle to keep the oral drug formulation (260) from premature drying. The humectant may include, but is in no way limited to glycerin, sorbitol, mannitol, or any other edible humectant. According to one exemplary embodiment, the humectant is present in the vehicle as glycerin in a concentration of up to approximately 5% of the vehicle by volume.

According to one exemplary embodiment, the vehicle component of the present oral drug formulation may also include other additives as desired including, but in no way limited to, driers, thinners, waxes, lubricants, reducing oils and solvents, body gum, binding varnish, antioxidants, anti-skinning agents, resins, and/or binders.

Additionally, the present oral drug formulation (260) may also include an edible colorant component according to one exemplary embodiment. Suitable colorants include any edible compounds, or combinations thereof, including, but in no way limited to, FD&C approved colorants. The aforementioned colorants may also be water-soluble, further facilitating their incorporation into a water-based oral drug formulation.

Exemplary Implementation and Operation

Figure 4:
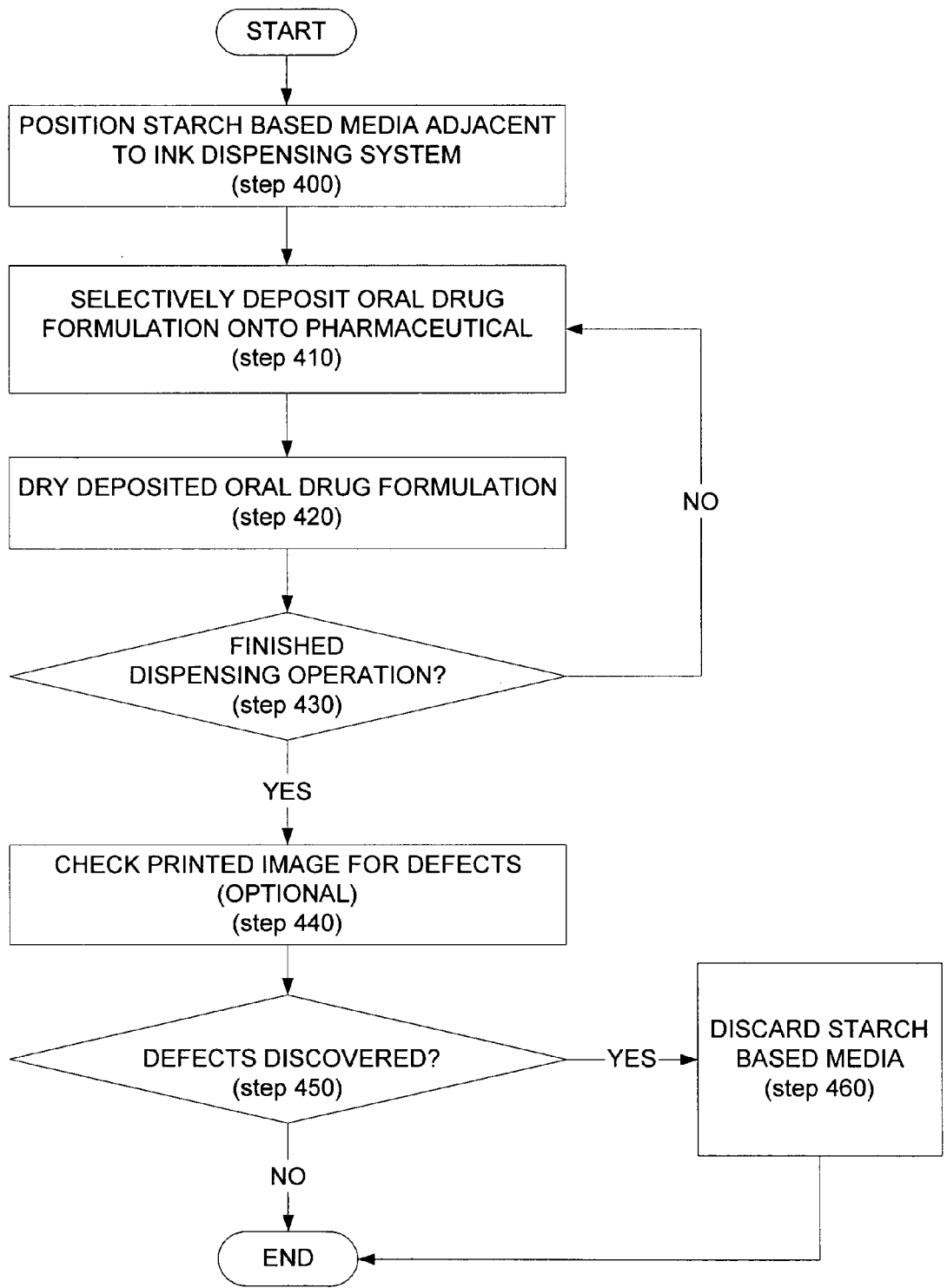
FIG. 4 is a flow chart illustrating a method for selectively depositing a known quantity of an oral drug formulation onto a starch based media, according to one exemplary embodiment.

Once the above-mentioned oral drug formulation (260; FIG. 2) is formed, it may be jetted onto a starch based media (270; FIG. 2) or other substrate to form a solid drug dosage. FIG. 4 illustrates an exemplary method for jetting an oral drug formulation onto a starch based media according to one exemplary embodiment. As shown in FIG. 4, the present method begins by positioning a starch based media under the present ink dispensing system (step 400). Once positioned, the ink dispensing system selectively deposits the oral drug formulation onto the starch based media (step 410) where it is subsequently absorbed (step 420). Upon deposition of the oral drug formulation onto the starch based media, a determination is made as to whether the present printing system (200; FIG. 2) has completed its drug formulation dispensing operation (step 430). If it is determined that the drug formulation dispensing operation is not complete (NO, step 430), the printing system again selectively jets an oral drug formulation onto the starch based media (step 410). If, however, the ink dispensing operation is complete (YES, step 430), the printed media is optionally examined for defects (step 440). If no defects are found (NO, step 450), the oral drug formulation dispensing process is complete. If, however, printing defects are found on the printed media (YES, step 450), the starch based media may be discarded (step 460) or otherwise reprocessed. The above-mentioned steps will now be described in further detail below.

As shown in FIG. 4, the present method for printing an oral drug formulation on a starch based media begins by positioning the starch based media under the dispensing system to facilitate reception of the oral drug formulation (step 400). As shown in FIG. 2, the starch based media (270) may be positioned under the dispensing system (200) by a moveable substrate (280). Alternatively, an operator or a number of mechanical transportation apparatuses may manually place the starch based media (270) adjacent to the dispensing system (200).

Once the starch based media (270) is correctly positioned, the present dispensing system (200) may be directed by the computing device (210) to selectively deposit the oral drug formulation (260) onto the starch based media (step 410; FIG. 4). As was mentioned previously, the desired dosage of the oral drug formulation to be printed on the starch based media (270) may initially be determined on a program hosted by the computing device (210). The program created dosage may then be converted into a number of processor accessible commands, which when accessed, may control the servo mechanisms (220) and the movable carriage (240) causing them to selectively emit a specified quantity of oral drug formulation (260) onto the starch based media (270). Precision of the resulting oral drug deposition may be varied by adjusting a number of factors including, but in no way limited to, the type of inkjet material dispenser (250) used, the distance between the inkjet material dispenser (250) and the starch based media (270), and the dispensing rate.

Once the oral drug formulation (260) has been selectively deposited onto the starch based media (270) according to the desired dosage, the deposited oral drug formulation may be absorbed by the starch based media (step 420; FIG. 4). When printed onto the starch based media (270) or other image receiving substrate, the various components of the oral drug formulation (260) enter the surface of the substrate or evaporate. Consequently, the oral drug formulation is affixed to the starch based media until consumption induces a selective release thereof.

Upon deposition and subsequent absorption, it is determined whether or not the oral drug formulation dispensing operation has been completed on the starch based media (step 430). Completion of the oral drug formulation dispensing operation may be evaluated by a system operator or by the coupled computing device (210). According to one exemplary embodiment, the computing device (210) determines whether sufficient oral drug formulation (260) has been dispensed to produce the desired dosage on the starch based media (270). If sufficient oral drug formulation (260) has not been dispensed (NO, step 430; FIG. 4), the dispensing system (200) continues to selectively deposit jetted oral drug formulation onto the starch based media (step 410; FIG. 4). If, however, sufficient oral drug formulation (260) has been dispensed (YES, Step 430; FIG. 4), the dispensed quantity may optionally be checked for defects (step 440). Adequacy of the volume of oral drug formulation dispensed may be evaluated by a number of flow-rate sensors (not shown) disposed on the inkjet material dispenser (250).

In order to check the printed media for defects (step 440), according to one exemplary embodiment, the starch based media (270) or other image receiving substrate may be analyzed according to weight, volume, or optical properties for obvious defects that may make the resulting substrate unacceptable. According to one exemplary embodiment, the starch based media (270) is subject to a series of optical scans configured to detect any alignment or deposition defects.

According to one exemplary embodiment, if defects are discovered on the printed media (YES, step 450; FIG. 4), the starch based media may be discarded (step 460; FIG. 4) and the system adjusted. If, however, no image defects are discovered (NO, step 450; FIG. 4) the starch based media (270) may be packaged or otherwise distributed.

According to one exemplary embodiment, the above mentioned process was used to produce a sample starch based media containing a desired dosage of oral drug formulation. According to the present exemplary embodiment, a solution of dimethylsulfoxide (DMSO): ethyl alcohol (EtOH): and glycerine in proportions of 80:17:3 (Volume/Volume) respectively was disposed by an inkjet dispenser onto the surface of a rice paper substrate manually placed adjacent to the inkjet material dispenser and on the surface of a coated rice paper substrate. According to this exemplary embodiment, the solution also included an API in the form of prednisolone in concentration of approximately 200 mg/mL. Five patterns of the solution measuring ⅛' by 4" were deposited with various inkjet dispensers. The samples were permitted to be absorbed and dry into the substrates for 2 hours at between 36-39 decrees Celsius. Once the samples were absorbed and dried, they were tested for dissolution rates using a dissolution apparatus at the following operating conditions: 50 RPM paddle speed from 0-60 minutes at a bath temperature of 37 degrees Celsius; and 250 RPM paddle speed from 61-120 minutes at a bath temperature 37 degrees Celsius. Samples of the dissolution rate were subsequently taken at the following time points: 5, 10, 20, 30, 45, 60, 65, and 120 minutes.

Figure 6:
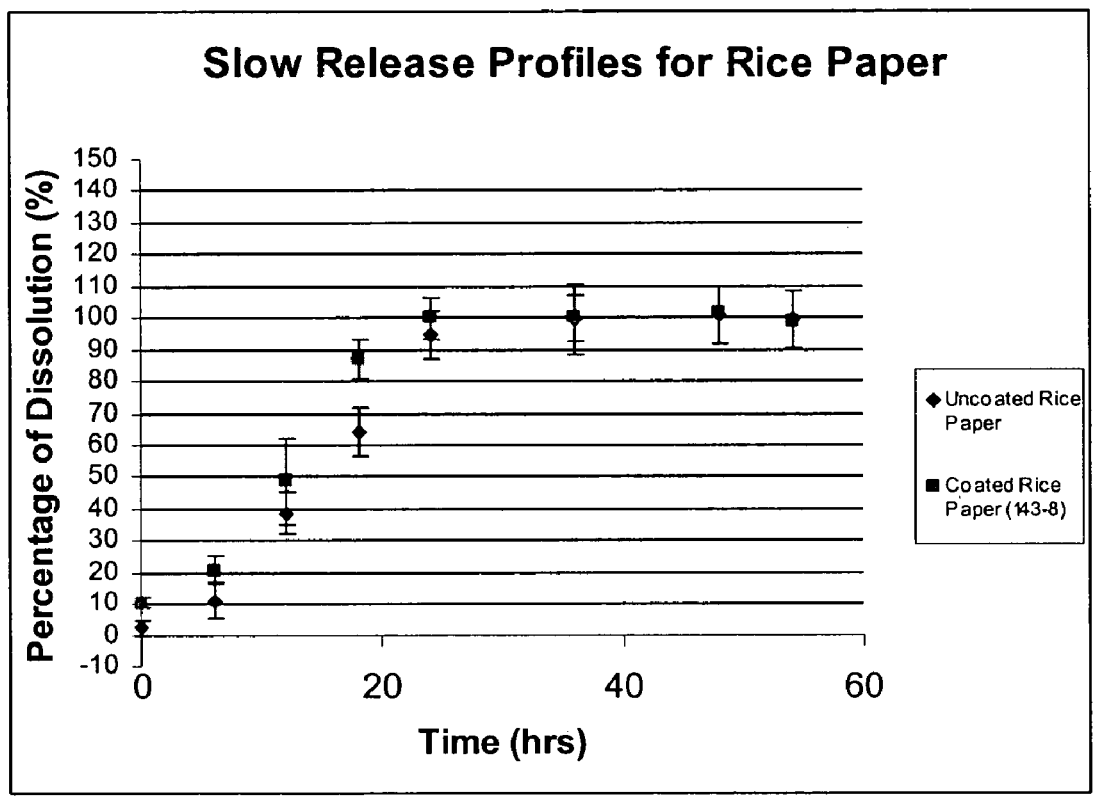
FIG. 6 is a graph illustrating a dissolution rate of a starch based media containing an oral drug formulation according to one exemplary embodiment.

Additionally, a second solution of the above-mentioned composition was disposed by an inkjet dispenser onto the surface of a rice paper substrate manually placed adjacent to the inkjet material dispenser and on the surface of a coated rice paper substrate. Again, five patterns of the solution measuring ⅛' by 4" were deposited with various inkjet dispensers. The samples were permitted to be absorbed and dry into the substrates for 2 hours at between 36-39 degrees Celsius. However, once the second set of samples were absorbed and dried, they were tested for dissolution rates using a dissolution apparatus at the following operating conditions: 50 RPM paddle speed from 0-54 hrs at a bath temperature of 37 degrees Celsius. Water was used as the dissolution media in the dissolution bath. Samples of the dissolution rate were subsequently taken at the following time points: 0, 6, 12, 18, 24, 36, 48, and 54 hours. FIG. 6 illustrates the results of the above-mentioned samples. As illustrated in FIG. 6, 100% of the above-mentioned API is released from the substrate after 24 hours under the above operating conditions.

Figure 5:
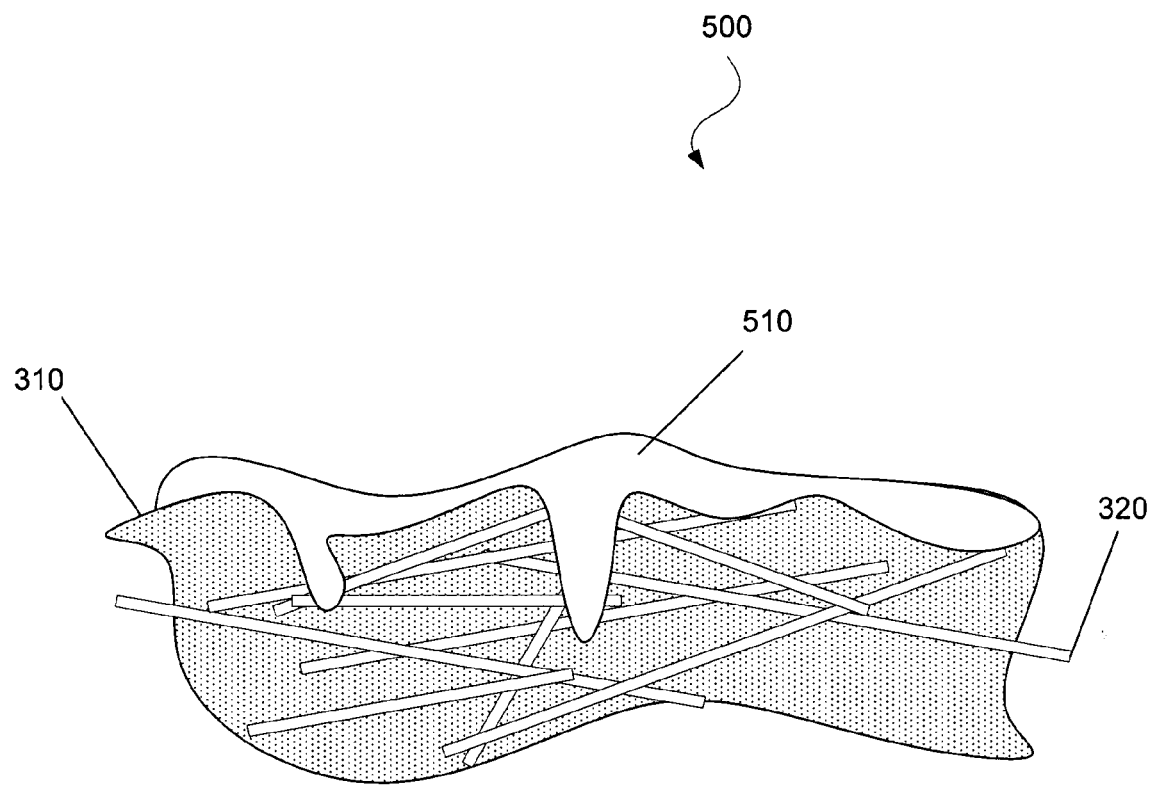
FIG. 5 is a perspective view illustrating the dissolving of a starch based media incorporating the present system and method when ingested, according to one exemplary embodiment.

As a result of the above-mentioned processes, the effectiveness of the present system and method has been demonstrated. As illustrated in FIG. 5, when the starch based media containing an oral drug formulation (500) is consumed or otherwise placed in contact with a dissolution liquid, the starch fibers (320) and granules absorb water or other liquid forms of the dissolution liquid (510) due to formation of hydrogen bonds between the starch (a polysaccharide) and water. This water absorption causes a swelling of the fibers (320) creating an interlocking network, which restricts the release of any absorbed oral drug formulation molecules. Additionally, the restricted flow of water or other dissolution liquid (510) within the starch fibers (320) restricts the flow of the oral drug formulation out to solution until the molecules of the starch fibers are broken down through time, temperature, and mixing.

A timed release of an oral drug formulation can be achieved using the present system and method by varying the rate of hydration of the starch fibers (320). According to one exemplary embodiment, uncoated rice paper releases between approximately 8 to 15% of the contained oral drug formulation per hour. However, the addition of a coating (310), as mentioned above, may be included to vary the release rate of the absorbed oral drug formulation. According to one exemplary embodiment, a higher release rate may be accomplished by including a coating (310). According to this exemplary embodiment, the main mechanism of dissolution for the first hour of a coated substrate is a dissolution of the coating (310) and any oral drug formulation that has been absorbed thereby. Once a substantial portion of the coating (310) has been dissolved by the dissolution liquid (510), the slower dissolution rate of the starch fibers (320) controls. The more easily the coating is dissolved and the lower the surface tension due to an increase of wetting of the fibers caused by the coating (310), the faster the starch based fibers are dissolved. Accordingly, the release rate of the oral drug formulation can be designed to have a varying release rate.

In conclusion, the present system and method for producing a slow-release oral dosage form decreases the design constraints inherent in forming a slow-release oral dosage, thereby reducing the overall cost of such a system. By incorporating the inkjetting of a desired oral drug formulation onto a starch based media, the present system and method allow for precise dosage distribution while controlling the dissolution rate of the drug formulation. Additionally, by varying the coating of the starch based media, greater control of the dosage distribution may be obtained.

The preceding description has been presented only to illustrate and describe exemplary embodiments of the present system and method. It is not intended to be exhaustive or to limit the system and method to any precise form disclosed. Many modifications and variations are possible in light of the above teaching. It is intended that the scope of the system and method be defined by the following claims.

What is claimed is:

1. A system for forming a slow release oral dosage of medication comprising:
   a computing device;
   an inkjet material dispenser communicatively coupled to said computing device;
   a starch based media disposed adjacent to said inkjet material dispenser, said starch based media having a coating configured to modify a rate of water uptake and subsequent dissolution of starch based fibers in said media; and
   a material reservoir fluidly coupled to said inkjet material dispenser, said material reservoir being configured to supply an oral dosage formulation to said inkjet material dispenser.

2. The system of claim 1, wherein said computing device comprises one of a personal computer, a laptop computer, a personal digital assistant, or a cellular telephone.

3. The system of claim 1, wherein said inkjet material dispenser comprises one of a thermally actuated inkjet dispenser, a mechanically actuated inkjet dispenser, an electrostatically actuated inkjet dispenser, a magnetically actuated dispenser, a piezo-electrically actuated inkjet dispenser, or a continuous inkjet dispenser.

4. The system of claim 1, wherein said starch based media comprises one of a polymeric organic film former or a paper organic film former.

5. The system of claim 4, wherein said starch based media comprises one of a rice starch based paper; a potato starch based paper; a functional derivative of starch, or a modified polysaccharide film.

6. The system of claim 5, wherein said functional derivative of starch comprises one of a cross-linked starch, an oxidized starch, an acetylated starch, a hydroxypropylated starch, a carboxymethylated starch, or a partially hydrolyzed starch.

7. The system of claim 5, wherein said modified polysaccharide film comprises one of a cellulose derivate, a starch hydrolysate, a pullulan, an alginate, a carragenan, or a pectin.

8. The system of claim 1, wherein said coating comprises an edible polymer.

9. The system of claim 8, wherein said edible polymer comprises one of a homopolymer of polyvinylphenol (PVP), a copolymer of PVP and polyvinylacetate, a crosslinked PVP particle, a copolymer of PVP and polyvinylacetate, a cationic PVP, a polyvinyl acetate (PVA) and PVA-polyethylene oxide (PEO) copolymer, a PVA-vinylacetal copolymer, a PVA-vinylacetal, a PVA-vinylamine copolymer, a poly vinyl methyl ether (PVME) homopolymer, a hydroxypropylmethylcellulose, a poly(2-ethyl oxazoline), a gelatin, or a methyl cellulose.

10. The system of claim 1, wherein said coating is configured to modify a release of said oral dosage.

11. The system of claim 1, wherein said oral dosage formulation comprises:
an oral drug component; and
a jettable vehicle component.

12. The system of claim 11, wherein said oral drug component comprises an insoluble drug.

13. The system of claim 11, wherein said oral drug component comprises one of an ace inhibitor, an antianxiety medication, a antihypertensive medication, a blood glucose regulator, an alzheimer-type dementia medication, an anorexiant, a central nervous system stimulant, an antidiuretic, a specific antidote, an antihistamine, an antipsychotic medication, an antimanic medication, a beta blocker, a calcium channel blocker, a contraceptive, a dermatologic, a diuretic, an estrogen, a progestin, an entrapyramidal movement disorder medication, a sedative, or a hypnotic medication.

14. The system of claim 13, wherein said oral drug component further comprises one of triazolam, felodipine, trandolapril, pergolide, rivastigmine tartrate, sibutramine hydrochloride, desmopressin acetate, flumazenil, desloratadine, risperidone, carvedilol, isradipine, norgestimate, methoxsalen, metolazone, estradiol, estrogens, conjugated estrogent, esterified cabergoline, zaleplon, or zolpidem tartrate.

15. The system of claim 11, wherein said oral drug component comprises one of Prednisolone, Glyburide, Lovastatin, Digoxin, or Nifedipine.

16. The system of claim 11, wherein said jettable vehicle further comprises:
an edible solvent;
a surfactant; and
humectants.

17. The system of claim 1, further comprising a servo mechanism configured to controllably move said inkjet dispensing device, said servo mechanism being communicatively coupled to said computing device.

18. The system of claim 1, further comprising a substrate disposed adjacent to said inkjet material dispenser, said substrate being configured to transport said starch based media.

19. A system for forming a slow release oral dosage of medication comprising:
a means for computing data;
a means for jetting material communicatively coupled to said computing means;
a starch based media disposed adjacent to said material jetting means, said starch based media having a coating configured to modify a rate of water uptake and subsequent dissolution of starch based fibers in said media, wherein said coating receives material dispensed to said media by said means for jetting material; and
a means for storing an oral dosage formulation, said formulation storage means being fluidly coupled to said material jetting means.

20. The system of claim 19, wherein said computing means comprises one of a personal computer, a laptop computer, a personal digital assistant, or a cellular telephone.

21. The system of claim 19, wherein said means for jetting material comprises an inkjet material dispenser.

22. The system of claim 19, wherein said starch based media comprises one of a polymeric or a paper organic film former.

23. The system of claim 19, wherein said starch based media comprises one of a rice starch based paper; a potato starch based paper; a functional derivative of starch, or a modified polysaccharide film.

24. The system of claim 19, wherein said coating comprises an edible polymer.

25. The system of claim 24, wherein said edible polymer comprises one of a homopolymer of polyvinylphenol (PVP), a copolymer of PVP and polyvinylacetate, a crosslinked PVP particle, a copolymer of PVP and polyvinylacetate, a cationic PVP, a polyvinyl acetate (PVA) and PVA-polyethylene oxide (PEO) copolymer, a PVA-vinylacetal copolymer, a PVA-vinylacetal, a PVA-vinylamine copolymer, a poly vinyl methyl ether (PVME) homopolymer, a hydroxypropylmethylcellulose, a poly(2-ethyl oxazoline), a gelatin, or a methyl cellulose.

26. The system of claim 19, wherein said oral dosage formulation comprises:
an oral drug component; and
a jettable vehicle component.

27. The system of claim 26, wherein said jettable vehicle further comprises:
an edible solvent;
a surfactant; and
humectants.

* * * * *

UNITED STATES PATENT AND TRADEMARK OFFICE
CERTIFICATE OF CORRECTION

| | | |
|---|---|---|
| PATENT NO. | : 7,900,577 B2 | |
| APPLICATION NO. | : 10/832702 | |
| DATED | : March 8, 2011 | |
| INVENTOR(S) | : Vanessa I. Chinea et al. | |

It is certified that error appears in the above-identified patent and that said Letters Patent is hereby corrected as shown below:

In column 11, line 12, in Claim 7, delete "carragenan" and insert -- carrageenan --, therefor.

In column 11, line 41, in Claim 13, delete "entrapyramidal" and insert -- extrapyramidal --, therefor.

In column 11, line 48, in Claim 14, delete "estrogent" and insert -- estrogen --, therefor.

Signed and Sealed this
Twentieth Day of December, 2011

David J. Kappos
*Director of the United States Patent and Trademark Office*